US008985773B2

(12) United States Patent
Umekawa

(10) Patent No.: US 8,985,773 B2
(45) Date of Patent: Mar. 24, 2015

(54) OPHTHALMOLOGIC APPARATUS AND OPHTHALMOLOGIC CONTROL METHOD, AND PROGRAM

(71) Applicant: Canon Kabushiki Kaisha, Tokyo (JP)

(72) Inventor: Kazuaki Umekawa, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 156 days.

(21) Appl. No.: 13/705,436

(22) Filed: Dec. 5, 2012

(65) Prior Publication Data
US 2013/0162950 A1    Jun. 27, 2013

(30) Foreign Application Priority Data

Dec. 21, 2011    (JP) .................................. 2011-279584

(51) Int. Cl.
*A61B 3/14*    (2006.01)
*A61B 3/00*    (2006.01)

(52) U.S. Cl.
CPC ............. *A61B 3/0033* (2013.01); *A61B 3/0075* (2013.01)
USPC ........................................................ 351/208

(58) Field of Classification Search
CPC .......... A61B 3/12; A61B 3/107; A61B 3/113; A61B 3/0075; A61B 3/1173
USPC .......... 351/208, 205, 206, 221, 212, 211, 246
See application file for complete search history.

(56) References Cited

U.S. PATENT DOCUMENTS

| 5,889,576 | A * | 3/1999 | Fujieda .......................... 351/208 |
| 6,409,344 | B1 * | 6/2002 | Hayashi ......................... 351/208 |
| 7,226,165 | B2 | 6/2007 | Maeda |
| 7,659,139 | B2 * | 2/2010 | Huang ............................ 438/99 |
| 7,695,139 | B2 | 4/2010 | Ishikura |
| 8,783,867 | B2 | 7/2014 | Muto |
| 2005/0105049 | A1 | 5/2005 | Maeda |
| 2006/0268230 | A1 | 11/2006 | Kogawa et al. |
| 2007/0146636 | A1 | 6/2007 | Ishikura |
| 2009/0180073 | A1 | 7/2009 | Ichikawa et al. |
| 2011/0199579 | A1 | 8/2011 | Muto |
| 2012/0220850 | A1 | 8/2012 | Umekawa |

FOREIGN PATENT DOCUMENTS

| CN | 1868397 A | 11/2006 |
| CN | 1989894 A | 7/2007 |
| CN | 101770282 A | 7/2010 |
| CN | 102160775 A | 8/2011 |
| JP | 2005-143903 A | 6/2005 |
| JP | 4428987 B2 | 3/2010 |
| KR | 10-2007-0070097 A | 7/2007 |

OTHER PUBLICATIONS

Aug. 11, 2014 Chinese Official Action in Chinese Patent Appln. No. 201210564135.1.

* cited by examiner

*Primary Examiner* — Hung Dang
(74) *Attorney, Agent, or Firm* — Fitzpatrick, Cella, Harper & Scinto

(57) ABSTRACT

Provided is an ophthalmologic apparatus that can perform the alignment of an acquiring unit with respect to an eye to be inspected without a rotation operation so that operability can be improved. The ophthalmologic apparatus includes: an acquiring unit which acquires specific information of an eye to be inspected; a joystick which can perform a rotation motion for moving the acquiring unit in an up-down direction, a left-right tilting motion for moving the acquiring unit in a left-right direction with respect to the eye to be inspected, and a front-back tilting motion for moving the acquiring unit in a front-back direction with respect to the eye to be inspected; and a control unit which changes a motion for moving the acquiring unit in the up-down direction from the rotation motion to the front-back tilting motion.

14 Claims, 7 Drawing Sheets

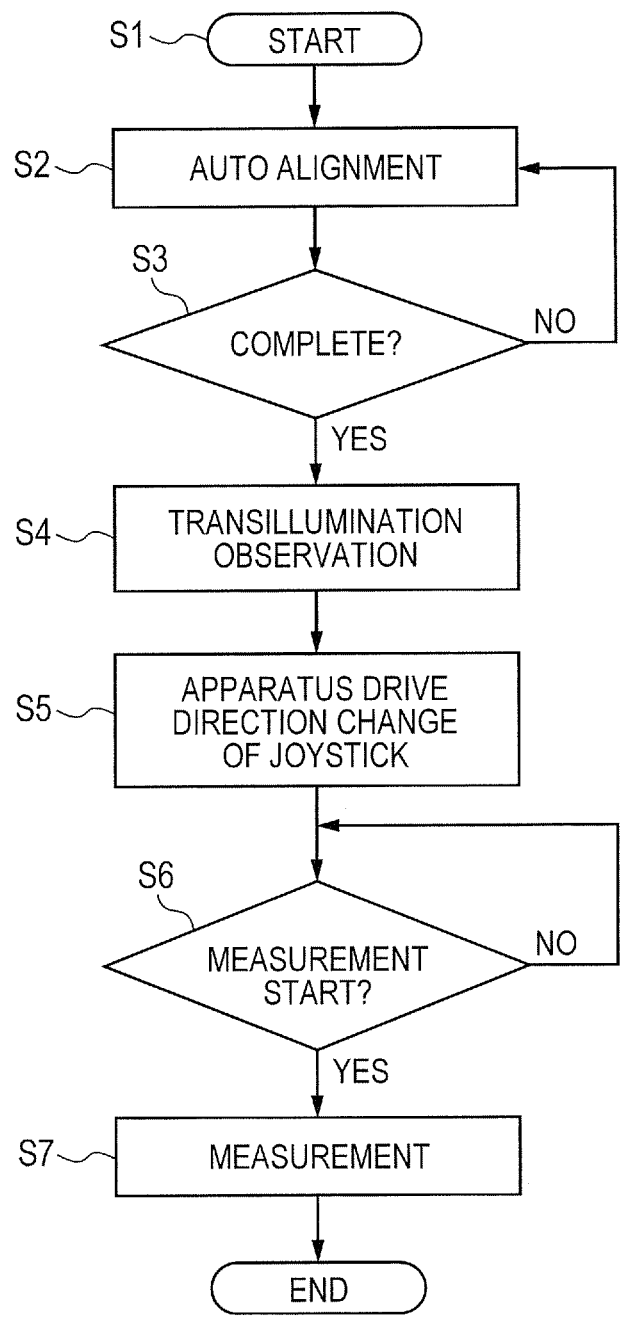

OPHTHALMOLOGIC APPARATUS AND OPHTHALMOLOGIC CONTROL METHOD, AND PROGRAM

BACKGROUND OF THE INVENTION

1. Field of the Invention

The present invention relates to an ophthalmologic apparatus and an ophthalmologic control method, and a program, for acquiring specific information of an eye to be inspected (for measuring, inspecting, or photographing eye characteristics).

2. Description of the Related Art

There is known a conventional ophthalmologic apparatus for measuring eye refractive power of an eye to be inspected, in which automatic adjustment (automatic alignment) is performed so that aligned states in front-back, left-right, and up-down directions of an acquiring unit (apparatus measuring portion) with respect to the eye to be inspected become within predetermined ranges. In this case, there is a case where although the alignment is completed, measurement cannot be performed correctly because of a disease such as cataract. In this case, it is known to move the measurement position manually from the center of pupil in the left-right direction and in the up-down direction so that multiple measurements are performed while searching for measurable positions.

Further, it is known to continue the automatic adjustment (automatic tracking) so that the aligned state of the acquiring unit with respect to the eye to be inspected becomes within a predetermined range only in the front-back direction, and to perform the adjustment by a manual operation in the left-right direction and in the up-down direction (see Japanese Patent No. 4428987).

However, the ophthalmologic apparatus described in Japanese Patent No. 4428987 has the following problem. An electronic joystick is used for the automatic tracking only in the front-back direction, and the alignment is performed manually in the left-right direction and in the up-down direction, and hence the operation includes a rotation motion that is hard to operate. Specifically, in the ophthalmologic apparatus described in Japanese Patent No. 4428987, in order to move the acquiring unit (apparatus measuring portion) in the left-right direction and in the up-down direction by using the joystick, it is necessary to tilt the joystick in the left-right direction while rotating the joystick. In addition, in order to perform the measurement while moving the acquiring unit in the left-right direction and in the up-down direction, it is necessary to press a switch disposed on the upper portion of the joystick while rotating the joystick.

SUMMARY OF THE INVENTION

It is an object of the present invention to solve the above-mentioned problem and to provide an ophthalmologic apparatus that can perform the alignment of an acquiring unit with respect to an eye to be inspected without a rotation operation so that operability can be improved.

In order to achieve the above-mentioned object, according to an exemplary embodiment of the present invention, there is provided an ophthalmologic apparatus, including: an acquiring unit which acquires specific information of an eye to be inspected; a joystick which can perform a rotation motion for moving the acquiring unit in an up-down direction, a left-right tilting motion for moving the acquiring unit in a left-right direction with respect to the eye to be inspected, and a front-back tilting motion for moving the acquiring unit in a front-back direction with respect to the eye to be inspected; and a control unit which changes a motion for moving the acquiring unit in the up-down direction from the rotation motion to the front-back tilting motion.

According to an exemplary embodiment of the present invention, there is provided an ophthalmologic apparatus, including: an acquiring unit which acquires specific information of an eye to be inspected; a joystick which can perform input for displacement in an up-down direction by a first motion of rotation, input for displacement in a left-right direction by a second motion of left-right tilting, and input for displacement in a front-back direction by a third motion of front-back tilting; a first drive system, a second drive system, and a third drive system which can drive the acquiring unit in the up-down direction, the left-right direction, and the front-back direction in response to the first motion, the second motion, and the third motion of the joystick, respectively, for displacing the acquiring unit with respect to the eye to be inspected; and a control unit which drives and controls the first drive system, the second drive system, and the third drive system, in which: the control unit has a first mode and a second mode; in the first mode, the control unit drives the first drive system, the second drive system, and the third drive system by the first motion, the second motion, and the third motion of the joystick, respectively; and in the second mode, the control unit inhibits driving of the first drive system by the first motion, controls the second drive system to drive by the second motion, and controls the first drive system to drive by the third motion, as a drive change.

Further, according to an exemplary embodiment of the present invention, there is provided an ophthalmologic control method, including: an acquiring step of acquiring, by an acquiring unit, specific information of an eye to be inspected; and a control step of changing a motion of a joystick, which can perform a rotation motion for moving the acquiring unit in an up-down direction, a left-right tilting motion for moving the acquiring unit in a left-right direction with respect to the eye to be inspected, and a front-back tilting motion for moving the acquiring unit in a front-back direction with respect to the eye to be inspected, for moving the acquiring unit in the up-down direction from the rotation motion to the front-back tilting motion.

In addition, an ophthalmologic control program also constitutes another exemplary embodiment of the present invention.

According to the exemplary embodiments of the present invention, the drive change of the joystick is performed, and hence it is possible to perform the alignment of the acquiring unit with respect to the eye to be inspected without the rotation operation so that operability can be improved.

Further features of the present invention will become apparent from the following description of exemplary embodiments with reference to the attached drawings.

BRIEF DESCRIPTION OF THE DRAWINGS

FIG. 9 is a flowchart of the eye refractometer meter according to a second embodiment of the present invention.

DESCRIPTION OF THE EMBODIMENTS

First Embodiment
(Entire Structure)

Figure 2:
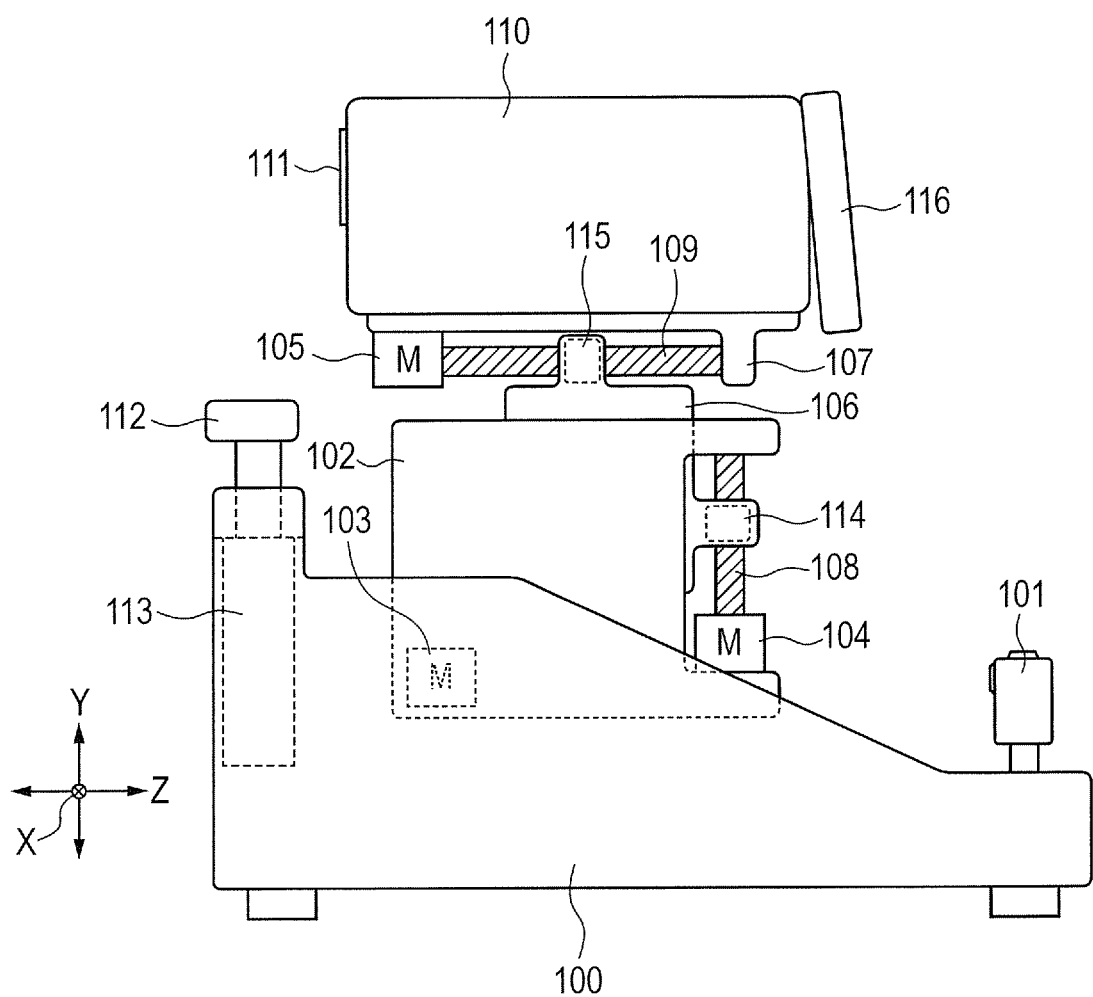
FIG. 2 is an outline diagram of an eye refractometer as an ophthalmologic apparatus according to embodiments of the present invention.

The present invention is described in detail based on illustrated embodiments. FIG. 2 illustrates a schematic structure of an eye refractometer as an ophthalmologic apparatus according to embodiments of the present invention. A frame 102 can move relative to a base 100 in a left-right direction (hereinafter referred to as X axis direction). A drive mechanism in the X axis direction is constituted of an X axis drive motor 103 fixed onto the base 100, a feed screw (not shown) connected to a motor output shaft, and a nut (not shown) fixed to the frame 102 so as to move along the feed screw in the X axis direction. When the motor 103 rotates, the frame 102 moves in the X axis direction via the feed screw and the nut.

A frame 106 can move relative to the frame 102 in an up-down direction (hereinafter referred to as Y axis direction). A drive mechanism in the Y axis direction is constituted of a Y axis drive motor 104 fixed onto the frame 102, a feed screw 108 connected to a motor output shaft, and a nut 114 fixed to the frame 106 so as to move along the feed screw in the Y axis direction. When the motor 104 rotates, the frame 106 moves in the Y axis direction via the feed screw and the nut.

A frame 107 can move relative to the frame 106 in a front-back direction (hereinafter referred to as Z axis direction). A drive mechanism in the Z axis direction is constituted of a Z axis drive motor 105 fixed onto the frame 107, a feed screw 109 connected to a motor output shaft, and a nut 115 fixed to the frame 106 so as to move along the feed screw in the Z axis direction.

When the motor 105 rotates, the frame 107 moves in the Z axis direction via the feed screw 109 and the nut. A measurement unit 110 as an acquiring unit for acquiring specific information of an eye to be inspected is fixed onto the frame 107. A light source (not shown) for performing alignment and a light source unit 111 for measuring corneal curvature are disposed on an end portion of the measurement unit 110 on a subject side. In addition, a joystick 101 as an operation member for aligning the measurement unit 110 with respect to an eye to be inspected E is disposed to the base 100. As described later, when the measurement is performed, the alignment can be performed by tilting the joystick 101.

When refractive power is measured, the subject puts his or her chin on a chin rest 112 and presses the forehead to a forehead rest portion of a face receiving frame (not shown) fixed to the base 100 so that a position of the eye to be inspected can be fixed. In addition, the chin rest 112 can be adjusted in the Y axis direction by a chin rest drive mechanism (chin rest drive motor) 113 depending on a size of the subject face. On an end portion of the measurement unit 110 on an inspector side, there is disposed an LCD monitor 116 as a display member for observing the eye to be inspected E, on which a result of the measurement and the like can be displayed.

(Eye Refractive Power Measurement Optical System)

Figure 3:
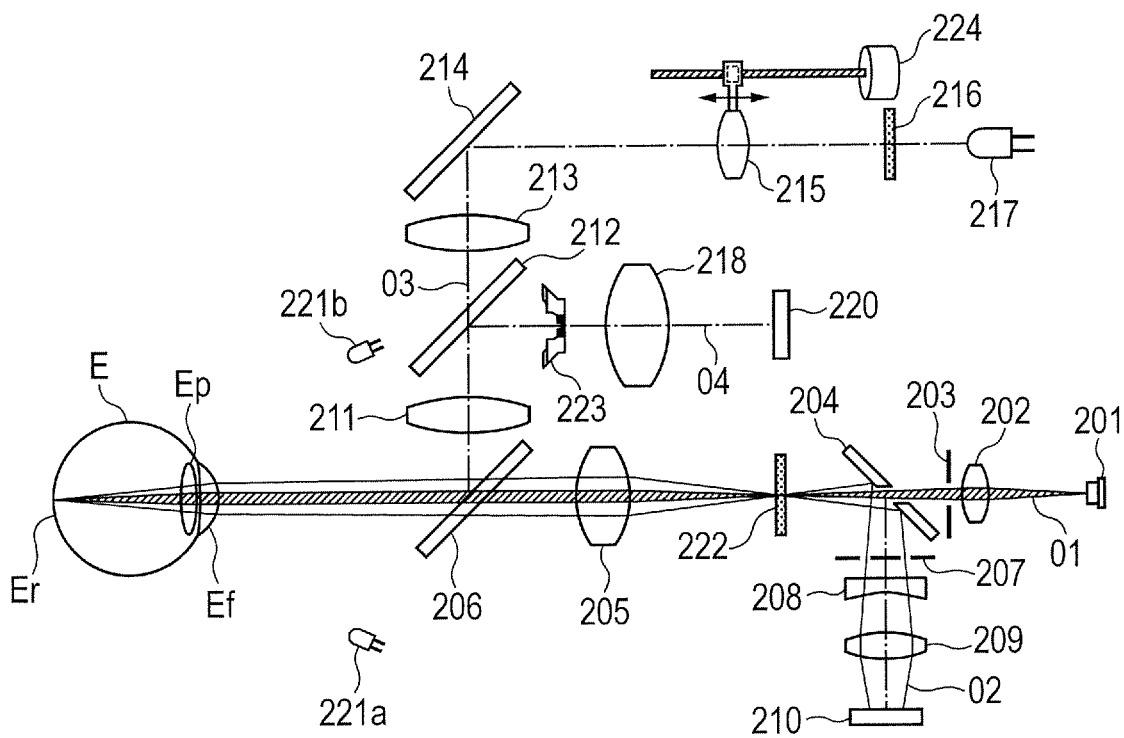
FIG. 3 is a layout diagram of a measurement optical system of the eye refractometer according to a first embodiment of the present invention.

FIG. 3 is a layout diagram of an eye refractive power measurement optical system in the measurement unit 110 according to a first embodiment of the present invention. Along an optical path 01 from a light source 201 emitting light of a wavelength of 880 nm for measuring eye refractive power to the eye to be inspected E, there are disposed a lens 202, a stop 203 substantially conjugate with a pupil Ep of the eye to be inspected E, a perforated mirror 204, and a lens 205 in the stated order. In addition, there is disposed a dichroic mirror 206 that totally reflects infrared and visible light of a wavelength of 880 nm or shorter and partially reflects light of a wavelength of 880 nm or longer from the eye to be inspected E side so as to be opposed to the eye to be inspected E.

In addition, along an optical path 02 in the reflection direction of the perforated mirror 204, there are disposed a stop 207 having an annular slit substantially conjugate with the pupil Ep, a beam spectral prism 208, a lens 209, and an image sensor 210 in the stated order.

The above-mentioned optical system is for measurement of eye refractive power. A beam emitted from the measuring light source 201 is decreased in its width by the stop 203 and is condensed as a first image formation by the lens 202 before the lens 205. Then, the beam passes through the lens 205 and the dichroic mirror 206, and reaches a pupil center of the eye to be inspected E. The beam is reflected by the fundus, and the fundus reflection light passes through the pupil center and enters the lens 205 again. The entering beam passes through the lens 205 and then is reflected by a periphery of the perforated mirror 204. The reflected beam is separated by pupil separation in the stop 207 substantially conjugate with the pupil Ep of the eye to be inspected E and the beam spectral prism 208, and is projected as a ring image to a light receiving plane of the image sensor 210.

If the eye to be inspected E is an emmetropic eye, this projected ring image becomes a predetermined circle. If the eye to be inspected E is a short-sighted eye, the projected circle becomes smaller than that in the emmetropic eye. If the eye to be inspected E is a long-sighted eye, the projected circle becomes larger than that in the emmetropic eye. If the eye to be inspected E has astigmatism, the projected ring image becomes an ellipse in which an angle formed between a horizontal axis and the ellipse is an astigmatism axis angle. Based on a coefficient of this ellipse, the refractive power is determined.

(Alignment Light Receiving Optical System and Fixation Target Projecting Optical System)

On the other hand, in the reflection direction of the dichroic mirror 206, there are disposed a fixation target projecting optical system and an alignment light receiving optical system used for both anterior ocular segment observation and alignment detection of the eye to be inspected. On an optical path 03 of the fixation target projecting optical system, there are disposed a lens 211, a dichroic mirror 212, a lens 213, a reflection mirror 214, a lens 215, a fixation target 216, and a fixation target illumination light source 217 in the stated order.

When guiding to the fixation target, a projection beam from the turned-on fixation target illumination light source 217 illuminates the fixation target 216 from the backside, and is projected to the fundus Er of the eye to be inspected E via the lens 215, the reflection mirror 214, the lens 213, the dichroic mirror 212, and the lens 211. Note that, the lens 215 can be moved in the optical axis direction by a fixation target guide motor 224 in order to perform eyesight guide of the eye to be inspected E so as to realize a fogging state.

In addition, on an optical path 04 in the reflection direction of the dichroic mirror 212, there are disposed an alignment prism stop 223 inserted and removed by an alignment prism stop insertion-and-removal solenoid (not shown), a lens 218, and an image sensor 220 in the stated order. By the insertion/removal of the alignment prism stop 223, the alignment can be performed when the alignment prism stop 223 is on the optical path 04, and the anterior ocular segment observation or transillumination observation can be performed when the alignment prism stop 223 is removed from the optical path 04.

Figure 4:
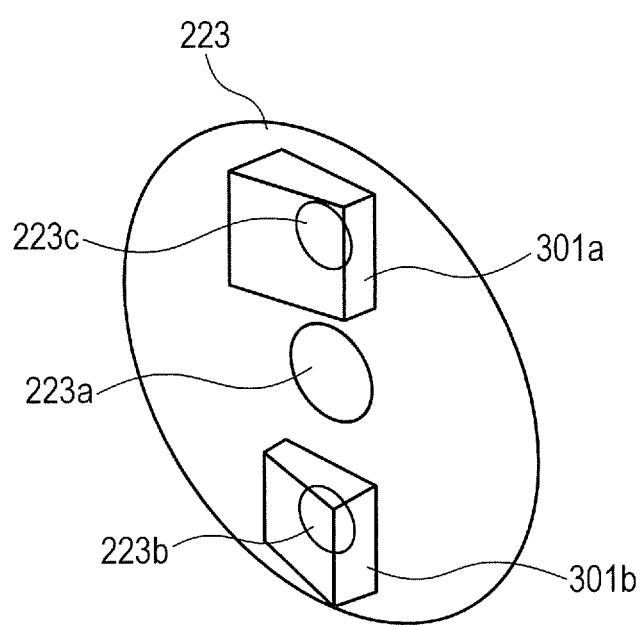
FIG. 4 is a perspective view of an alignment prism stop of the measurement optical system.

Now, FIG. 4 illustrates a shape of the alignment prism stop 223. Three openings 223a, 223b, and 223c are formed in a disk-like stop plate, and alignment prisms 301a and 301b that transmit only a beam of a wavelength of around 880 nm are attached to the dichroic mirror 212 side of the openings 223c and 223b on both sides.

Referring back to FIG. 3, anterior ocular segment illumination light sources (extraocular illumination light sources) 221a and 221b having a wavelength of approximately 780 nm are disposed diagonally in front of an anterior ocular segment of the eye to be inspected E. A beam from the anterior ocular segment of the eye to be inspected illuminated by the anterior ocular segment illumination light sources 221a and 221b forms an image on the light receiving sensor plane of the image sensor 220 via the dichroic mirror 206, the lens 211, the dichroic mirror 212, and the center opening 223a of the alignment prism stop.

The light source for the alignment detection also works as the measuring light source 201 for the eye refractive power measurement. When the alignment is performed, a translucent diffusion panel 222 is inserted in the optical path by a diffusion panel insertion-and-removal solenoid (not shown).

A position at which the diffusion panel 222 is inserted is substantially a primary imaging position of the measuring light source 201 by the projection lens 202 and is a focal position of the lens 205. Thus, an image of the measuring light source 201 is temporarily formed on the diffusion panel 222 and becomes a secondary light source, which is projected from the lens 205 toward the eye to be inspected E as a thick collimated beam.

This collimated beam is reflected by a cornea Ef of the eye to be inspected so as to form a bright spot image, and the beam is partially reflected by the dichroic mirror 206 again. Then, the beam is reflected by the dichroic mirror 212 via the lens 211, passes through the opening 223a of the alignment prism stop and the alignment prisms 301a and 301b, and is converged by the lens 218 to form an image on the image sensor 220.

The center opening 223a of the alignment prism stop 223 transmits beams having a wavelength of 780 nm or longer from the anterior ocular segment illumination light sources 221a and 221b. Therefore, the reflection beams of an image of the anterior ocular segment illuminated by the anterior ocular segment illumination light sources 221a and 221b pass through the observation optical system and form images on the image sensor 220 by the imaging lens 218 via the opening 223a of the alignment prism stop 223 similarly to the path of the reflection beam of the cornea Ef.

In addition, the beam after passing through the alignment prism 301a is refracted downward, and the beam after passing through the alignment prism 301b is refracted upward. As described later, based on a positional relationship between the beams via the stops, the alignment of the eye to be inspected E can be performed.

(System Control Unit)

Figure 5:
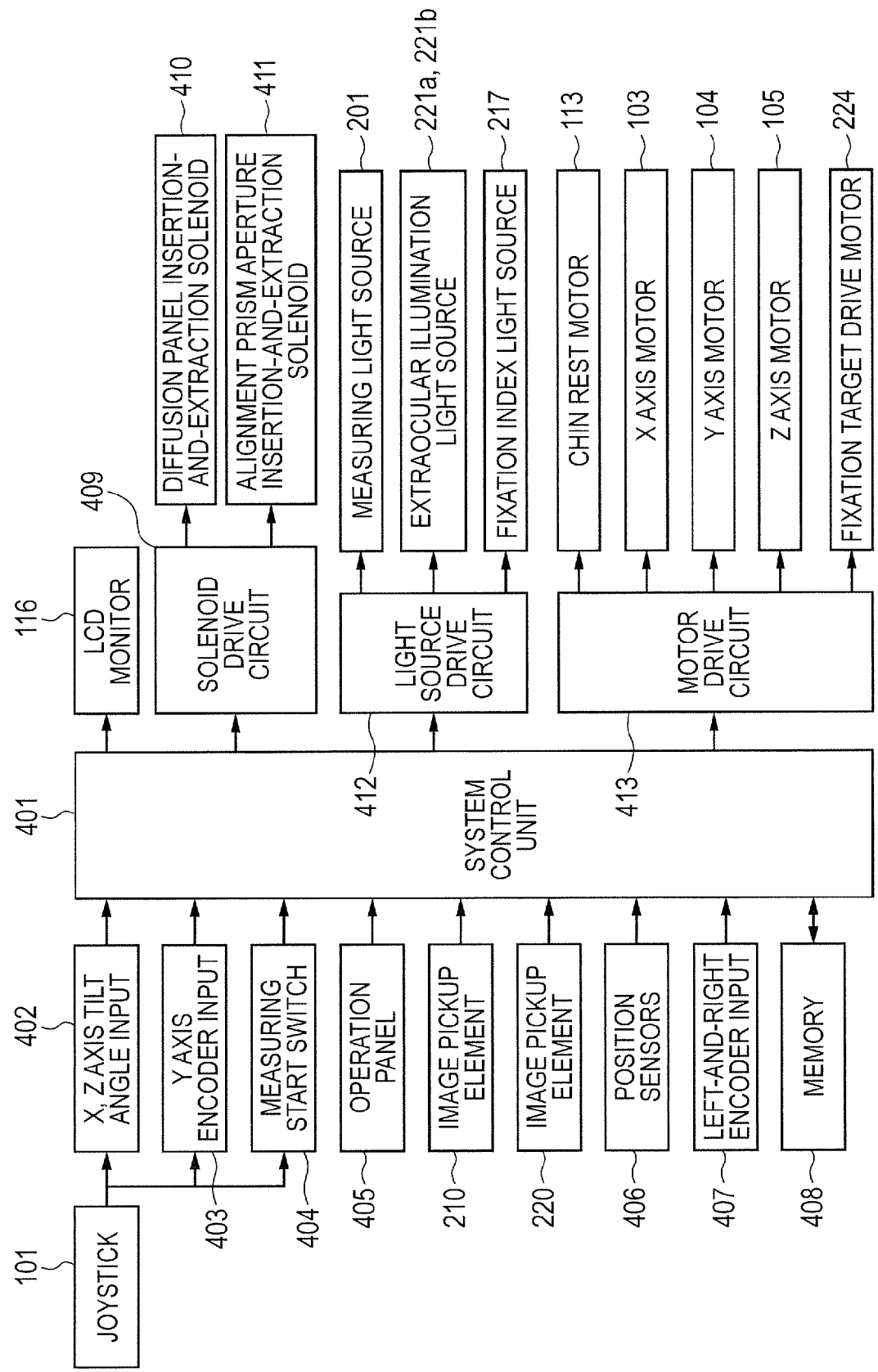
FIG. 5 is a system block diagram of the eye refractometer according to the first embodiment of the present invention.

FIG. 5 is a system block diagram. A system control unit 401 for controlling the entire system includes a program storage unit, a data storage unit storing data for correcting an eye refractive power value, an input and output control unit for controlling input and output with respect to various devices, and a processor for processing data obtained from various devices.

The system control unit 401 is connected to the joystick 101 for aligning the measurement unit 110 with respect to the eye to be inspected E and for starting the measurement, and is supplied with a tilt angle input 402 when the joystick 101 is tilted in the front-back and left-right directions, and an encoder input 403 when the joystick 101 is rotated. In addition, the system control unit 401 is supplied with a measuring start switch input 404 when a measuring start switch is pressed. In addition, on an operation panel 405 (disposed on the base 100 illustrated in FIG. 2), there are disposed a print button and a chin rest up-down switch, and the like. When the switch signal is input, the signal is sent to the system control unit 401.

An anterior ocular segment image of the eye to be inspected E photographed by the image sensor 220 is stored in a memory 408. A pupil and corneal reflex image of the eye to be inspected E is extracted from the image stored in the memory 408, and the alignment detection is performed. In addition, the anterior ocular segment image of the eye to be inspected E photographed by the image sensor 220 is combined with data of characters and graphics, and then the anterior ocular segment image, a measurement value, and the like are displayed on the LCD monitor 116.

The ring image for calculating the eye refractive power photographed by the image sensor 210 is stored in the memory 408. Each of solenoids 410 and 411 is driven and controlled by an instruction from the system control unit 401 via a solenoid drive circuit 409. In addition, the X axis motor 103, the Y axis motor 104, the Z axis motor 105, the chin rest motor 113, and the fixation target guide motor 224 are driven by instructions from the system control unit 401 via a motor drive circuit 413.

The measuring light source 201, the extraocular illumination light sources 221a and 221b, and the fixation target light source 217 are controlled by instructions from the system control unit 401 via a light source drive circuit 412 about turning on and off and changing intensity of light.

(First Mode/Manual Alignment Mode Related to Joystick)

An inspector uses the joystick 101 and performs input for a displacement in the up-down direction (Y direction) by a first motion of rotation, and performs input for a displacement in the left-right direction and in the front-back direction by a second motion of tilting in the left-right direction and a third motion of tilting in the front-back direction, respectively. Further, in response to the inputs of the joystick 101 in the up-down direction, the left-right direction, and the front-back direction, the system control unit 401 and the motor drive circuit 413 can drive the motors 104, 103, and 105 as drive systems, respectively.

In other words, by driving the motor 104 as a first drive system, the motor 103 as a second drive system, and the motor 105 as a third drive system, the measurement unit 110 as the acquiring unit can be displaced in the up-down direction, in the left-right direction, and in the front-back direction, respectively.

The manual alignment mode is used as a rough alignment mode. After aligning the measurement unit 110 as the acquiring unit with respect to the eye to be inspected to a certain extent, the inspector presses the predetermined measuring start switch so as to proceed to an automatic alignment mode described below.

(Third Mode/Automatic Alignment Mode without Relation to Joystick)

Figure 6:
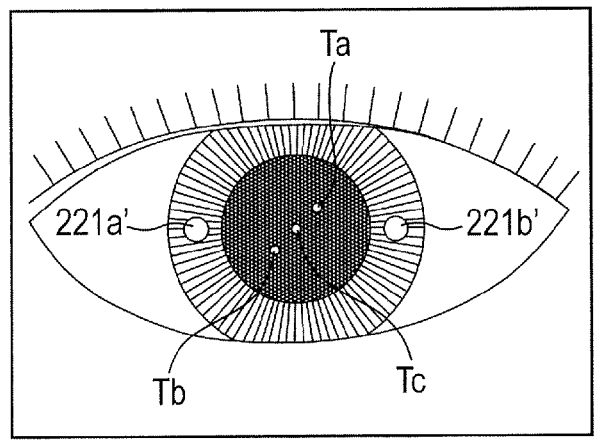
FIG. 6 is an explanatory diagram of an image of an anterior ocular segment including a corneal reflex image as a target for an alignment.

In the automatic alignment mode, the motor drive circuit 413 as the control unit automatically controls the Y axis motor 104, the X axis motor 103, and the Z axis motor 105 independently of the joystick until aligned states of the acquiring unit with respect to the eye to be inspected in the up-down, left-right, and front-back directions become constant, respectively. The alignment operation is described below. FIG. 6 shows an example of the anterior ocular segment image displayed on the LCD monitor 116 in the automatic alignment mode. As shown in FIG. 6, a cornea bright spot image formed by a cornea Ec is split by the openings 223a, 223b, and 223c of the alignment prism stop 223 and the prisms 301a and 301b in the alignment operation. Then, cornea bright spots Ta, Tb, and Tc as target images are photographed by the image sensor 220 together with the eye to be inspected E illuminated by the extraocular illumination light sources 221a and 221b and bright spot images 221a' and 221b' of the extraocular illumination light sources 221a and 221b.

The beam after passing through the alignment prism 301a illustrated in FIG. 4 is refracted in the left direction, while the beam after passing through the alignment prism 301b is refracted in the right direction, and hence the three bright spots Ta, Tb, and Tc can be acquired.

In addition, when the three cornea bright spots Ta, Tb, and Tc are detected, the system control unit 401 controls the motor drive circuit 413 so as to first drive the measurement unit 110 in the up-down and left-right directions so that the center bright spot Tc is aligned with the center direction as the automatic alignment mode. Next, the system control unit 401 drives the measurement unit 110 in the front-back direction so that the cornea bright spots Ta and Tb are aligned with respect to the cornea bright spot Tc in the horizontal direction (the lateral direction or the left-right direction). Then, the alignment is completed in a state where the three cornea bright spots Ta, Tb, and Tc are aligned in the horizontal direction.

Note that, the alignment prism stop 223 is disposed so that the individual stops are aligned in the vertical direction on the optical path as illustrated in FIG. 3, but the individual stops may be aligned in the horizontal direction. In this case, the beams are refracted by the corresponding prisms in the up-down direction, and the three bright spots are aligned in the up-down direction when the alignment of the measured portions in the front-back direction is completed.

(Measurement in Automatic Alignment Mode)

In order to measure the eye refractive power, the system control unit 401 removes the diffusion panel 222, which was inserted in the optical path 01 for the automatic alignment, from the optical path 01. Light intensity of the measuring light source 201 is adjusted, and the measurement beam is projected to the fundus Er of the eye to be inspected E. Then, the reflection light from the fundus propagates along the optical path 02 and is received by the image sensor 210. The photographed fundus image is projected in a ring shape by the refractive power of the eye to be inspected and by the ring stop 207. This ring image is stored in the memory 408. Barycentric coordinates of the ring image stored in the memory 408 are calculated, and an ellipse equation is determined by a well-known method. A long diameter, a short diameter, and a tilt angle of the major axis of the determined ellipse are calculated so that the eye refractive power of the eye to be inspected E is calculated.

Based on the determined eye refractive power value, the fixation target guide motor 224 is driven by the motor drive circuit 413 to a position corresponding to the refractive power value, and the lens 215 is moved so that the fixation target 216 is presented to the eye to be inspected E at refractivity corresponding to refractivity of the eye to be inspected E. After that, the lens 215 is moved by a predetermined amount to the far side so that the fixation target 216 is fogged, and the measuring light source is turned on again so as to measure the refractive power. In this way, the measurement of the refractive power, the fogging operation by the fixation target 216, and the measurement of the refractive power are repeated, and hence a final measurement value can be obtained, in which the refractive power becomes stable.

(Second Mode/Automatic Tracking Mode Related to Joystick)

Figure 7A:
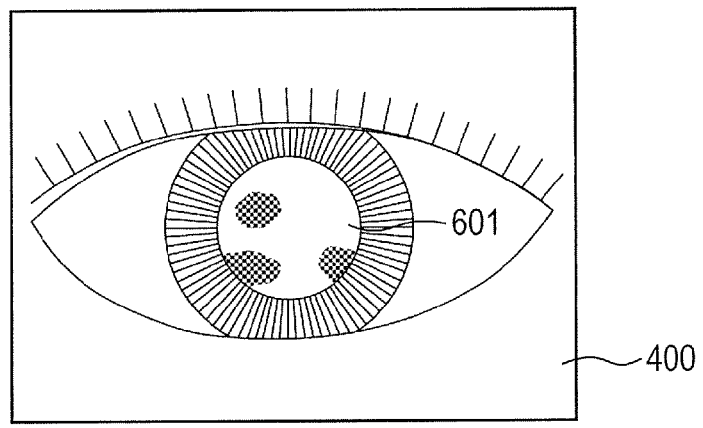
FIG. 7A shows a transillumination image in a case where a crystalline lens has opacity.
Figure 7B:
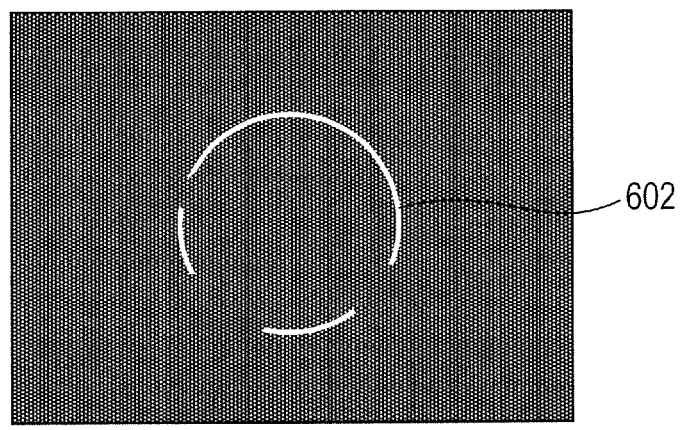
FIG. 7B shows a ring image photographed in the case where the crystalline lens has opacity.

The measurement of the eye refractive power is usually finished by measurement in the automatic alignment mode. However, in a case of an eye to be inspected having opacity in the crystalline lens, the projection beam from the measuring light source 201 does not reach the fundus Er because of the opacity, and hence the measurement cannot be performed because an image of reflection light cannot be acquired by the image sensor 210. In addition, in an eye to be inspected 601 having opacity as shown in FIG. 7A, even if the projection beam reaches the fundus Er, the reflection light is blocked by the opacity. As a result, as shown in FIG. 7B, a part of a ring image 602 for calculating the refractive power drops out or is blurred so that only a measurement result with low reliability can be obtained. Note that, FIG. 7A shows an example of the anterior ocular segment image displayed on the LCD monitor 116 in the same format as in FIG. 6, and FIG. 7B shows an example of the ring image 602 displayed on the LCD monitor 116.

Therefore, the measurement mode automatically proceeds to an automatic tracking mode described below if the ring image for calculating the eye refractive power cannot be obtained or if a part of the ring image drops out or is blurred so that a correct measurement result cannot be obtained in the measurement in the automatic alignment mode. In addition, the measurement mode automatically proceeds to the automatic tracking mode described below also in the case where the alignment with respect to the eye to be inspected has not become within a predetermined range (in a case where the automatic alignment has not been completed) because of nystagmus or corneal abnormalities.

In the automatic tracking mode, the system control unit 401 and the motor drive circuit 413 automatically continue to maintain a constant aligned state of the acquiring unit in the front-back direction with respect to the eye to be inspected. In other words, the Z axis motor 105 (the third drive system for moving in the front-back direction) is automatically controlled as automatic tracking control independently of the joystick.

Figure 8:
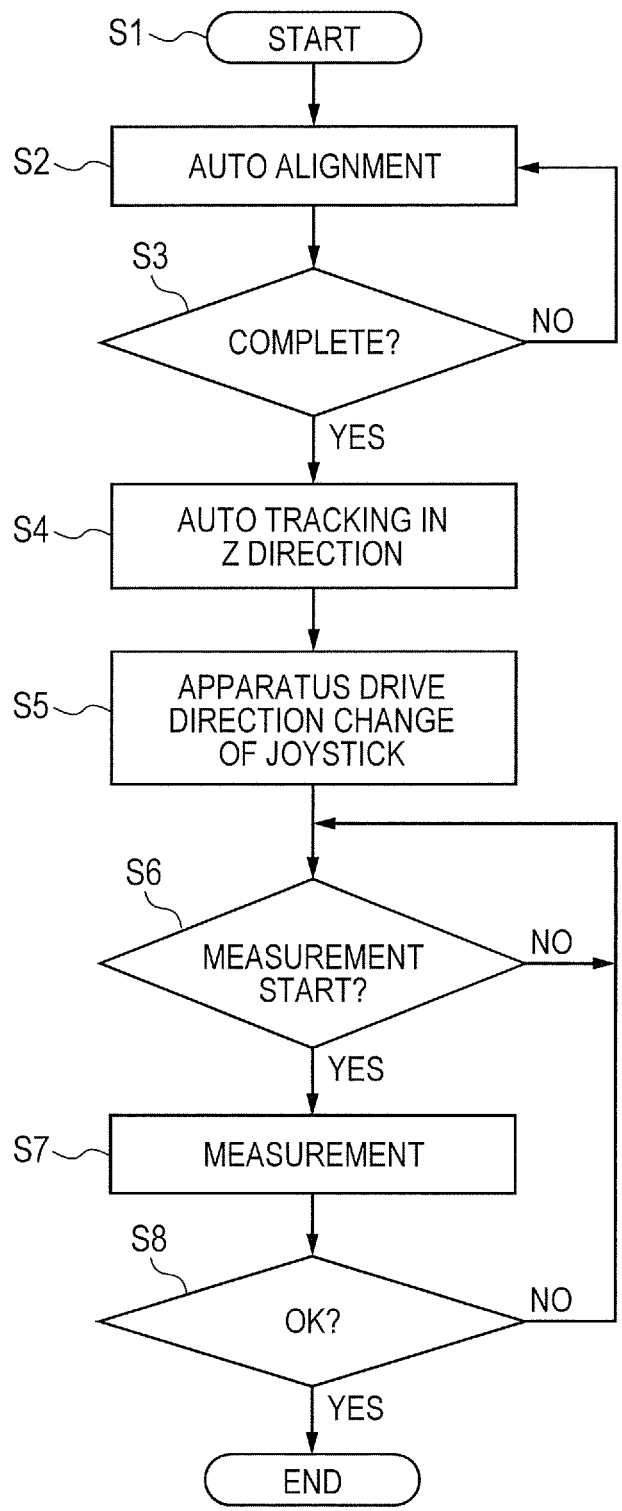
FIG. 8 is a flowchart of the eye refractometer according to the first embodiment of the present invention.

FIG. 8 illustrates a flowchart in which the manual alignment mode, the automatic alignment mode, and the automatic tracking mode are performed in the stated order to reach completion of the measurement. In Step S1, the inspector urges the subject to put his or her chin on the chin rest 112 and adjusts a position of the eye to be inspected in the Y axis direction (up-down direction) to be a predetermined height by the drive mechanism 113. The inspector operates the joystick 101 (in the manual alignment mode) to such a position that the corneal reflex image of the eye to be inspected E displayed on the LCD monitor 116 is displayed, and presses the measuring start switch.

When the measuring start switch is pressed, the automatic alignment in Step S2 is started. The corneal reflex image is extracted from the anterior ocular segment image of the eye to be inspected E stored in the memory 408, and the alignment is performed by the above-mentioned alignment method. In Step S3, it is determined whether or not the alignment is completed. When it is determined that the alignment is completed, the process proceeds to Step S4. When it is determined that the alignment is not completed, the process returns to Step S3.

When the alignment is completed, the automatic tracking is started only in the front-back direction by the above-mentioned alignment method in Step S4. Further, the fact the automatic tracking is being performed is displayed in a corner 400 of the LCD monitor 116 (FIG. 7A) by using an icon, for example.

(Drive Change in Automatic Tracking Mode)

Figure 1:
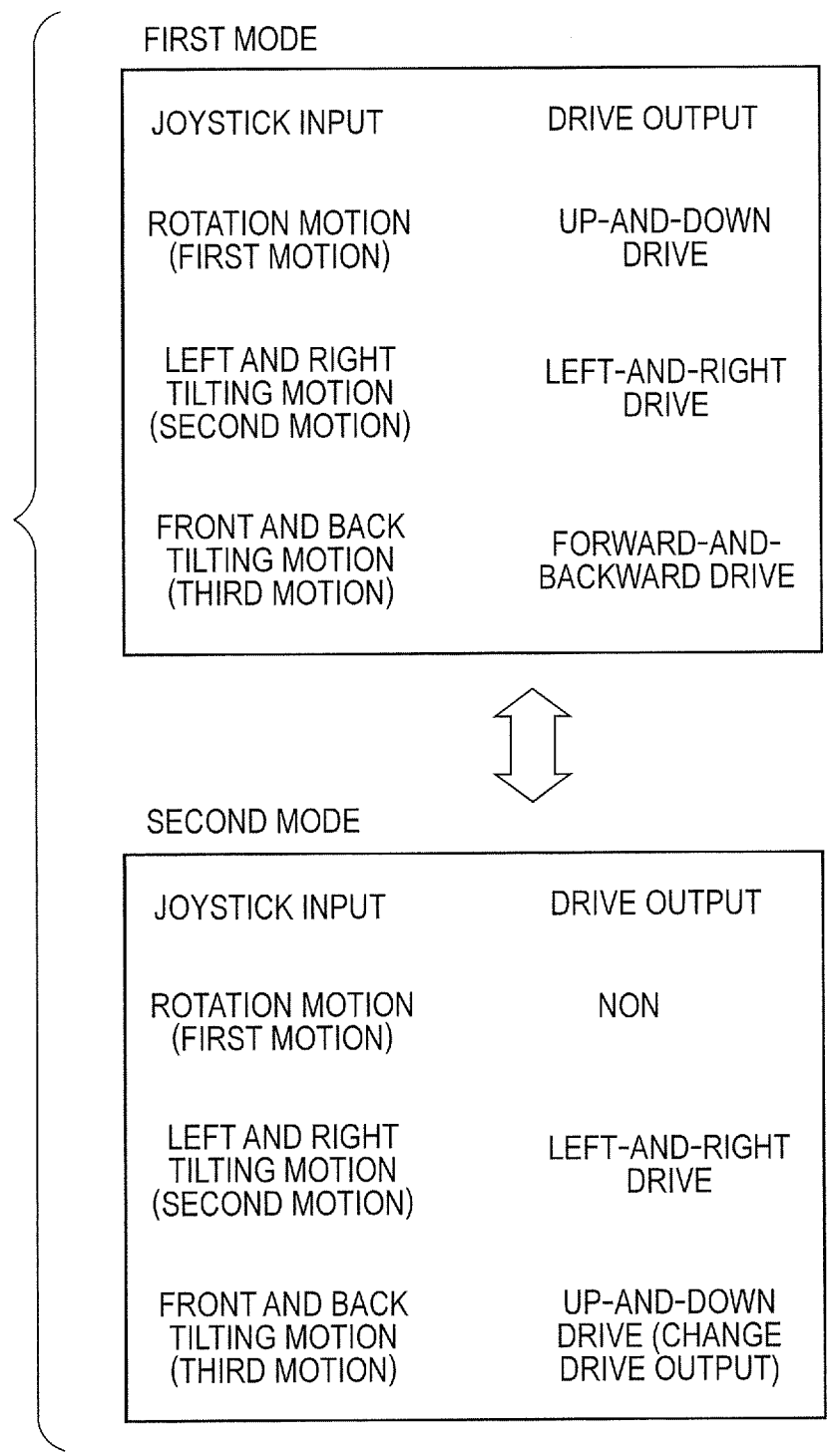
FIG. 1 is a diagram illustrating a first mode and a second mode of a control unit for driving and controlling first, second, and third drive systems that can move an acquiring unit in an up-down direction, a left-right direction, and a front-back direction in response to first, second, and third motions of a joystick, respectively.

In Step S5, the system control unit 401 and the motor drive circuit 413 perform input change of a drive signal for the motor in the control unit so that the measurement unit 110 is moved in the up-down direction when the joystick 101 is tilted in the front-back direction. In addition, a drive direction of the joystick 101 is changed so as to prevent the measurement unit 110 from moving in the up-down direction by rotation of the joystick 101. FIG. 1 illustrates a first mode in which the drive direction is not changed and a second mode in which the drive direction is changed. The drive direction change can be easily performed by the input change of the drive signal for the motor.

Specifically, before the drive change, the system control unit 401 and the motor drive circuit 413 transmit input signals from the X and Z axis tilt angle input 402 to the motor control unit 413 so that the X axis motor 103 and the Z axis motor 105 are driven. In addition, an input signal from the Y axis encoder input 403 is transmitted to the motor control unit 413 so that the Y axis motor 104 is driven. When the drive change is performed, the system control unit 401 and the motor drive circuit 413 transmit the input signals from the X and Z axis tilt angle input 402 to the motor control unit 413. Then, the X axis motor 103 and the Y axis motor 104 are driven, and the input signal from the Y axis encoder input 403 is prevented from being transmitted to the motor control unit 413. Note that, it is preferred to display a display form indicating the drive change in the corner 400 of the LCD monitor 116 (FIG. 7A), for example, during the drive change of the joystick according to this embodiment. Thus, the user can visually identify the current change of the joystick drive so that an operation error can be prevented.

In Step S6, it is determined whether or not the inspector tilts the joystick 101 so as to move the measurement position in the left-right and up-down directions and presses the measurement switch on the joystick 101 so as to start the measurement. When it is determined that the measurement is started, the process proceeds to Step S7. In Step S7, the measurement is performed by the above-mentioned eye refractive power measurement method, and the ring image and the measurement value are stored in the memory 408. In Step S8, it is determined whether or not the measurement error has occurred. When it is determined that a measurement error has occurred, the process returns to Step S6, and the measurement is performed again. When it is determined that the measurement error has not occurred, the automatic tracking is stopped, the drive direction of the joystick 101 is reset, and the measurement is finished.

The measurement is finished when the measurement error has not occurred in the above-mentioned measurement flow, but it is possible to adopt a configuration in which the measurement is finished when the measurement value is obtained a predetermined number of times, or when an automatic tracking cancel switch (not shown) is pressed. It is also possible to inform the inspector by buzzer sound (not shown) when starting the automatic tracking and when stopping the automatic tracking.

In addition, it is possible to stop the automatic tracking mode when the acquiring unit is moved beyond a predetermined range with respect to the eye to be inspected or when an operation other than a predetermined operation is performed. As examples of the former case, there is a case where the three cornea bright spots Ta, Tb, and Tc to be used for the automatic tracking cannot be detected, or a case where a measurement point is moved to the outside of the pupil. As examples of the latter case, there is a case where the joystick is rotated. In addition, the apparatus drive direction of the joystick is changed in Step S5 in the above-mentioned flow, but it is possible to adopt a configuration in which it can be selected by a setting whether or not to change the drive direction.

According to this embodiment, the inspector can easily identify a measurement position where the measurement can be performed by changing the drive direction even if the eye to be inspected has opacity in the crystalline lens.

Second Embodiment

A second embodiment of the present invention has a feature of having an input unit for switching from the first mode in which the drive direction is not changed to the second mode in which the drive direction is changed. Here, it is supposed that the left-right direction drive is performed by the left-right tilting motion, while the front-back direction drive is performed by the front-back tilting motion in the first mode, and then the input unit is used to act. In this case, the mode becomes the second mode in which the function of the front-back tilting motion is changed as described below. Specifically, the second mode is performed in a state where the transillumination observation of pupil of the eye to be inspected is performed, and the left-right direction drive is performed by the left-right tilting motion. On the other hand, the drive change is performed so that not the front-back direction drive but the up-down direction drive is performed by the front-back tilting motion.

FIG. 9 is a flowchart of this embodiment in which Step S4 (changing to the transillumination observation) is provided instead of Step S4 of FIG. 8 (automatic tracking only in the Z direction). In Step S1 of FIG. 9, the inspector urges the subject to put his or her chin on the chin rest 112 and adjusts a position of the eye to be inspected in the Y axis direction to be a predetermined height by the drive mechanism 113 in the manual alignment mode.

In addition, the inspector operates the joystick 101 to such a position that the cornea bright spot (target reflection image) of the eye to be inspected E displayed on the LCD monitor 116 is displayed, and presses the measuring start switch. When the measuring start switch is pressed, the automatic alignment in Step S2 is started so as to proceed to the automatic alignment mode. The corneal reflex image is extracted from the anterior ocular segment image of the eye to be inspected E stored in the memory 408, and the alignment is performed by the above-mentioned alignment method.

In Step S3, it is determined whether or not the alignment is completed. When it is determined that the alignment is completed, the process proceeds to Step S4. When it is determined that the alignment is not completed, the process returns to Step S3. When the alignment is completed, the alignment prism stop 223 is removed from the optical path for performing the transillumination observation in Step S4, and hence the transillumination observation can be performed.

In Step S5, similarly to Step S5 illustrated in FIG. 8 of the first embodiment, the system control unit 401 and the motor drive circuit 413 perform drive change so that the measurement unit 110 is moved in the up-down direction by tilting the joystick 101 in the front-back direction. In addition, the system control unit 401 and the motor drive circuit 413 perform drive change so that the measurement unit 110 is not moved in the up-down direction when the joystick 101 is rotated.

In Step S6, it is determined whether or not the inspector operates the joystick 101 so as to move the measurement position in the left-right and up-down directions, and presses the measuring start switch on the joystick 101 so as to start the measurement. When it is determined that the measurement is started, the process proceeds to Step S7. In Step S7, the measurement is performed by the above-mentioned eye refractive power measurement method, and the ring image, the measurement value, and the transillumination observation image are stored in the memory 408. Then, the measurement is finished. When a measurement error occurs, the measurement can be performed again by pressing the measurement start switch again.

In order to perform the automatic alignment again, it is possible to press an automatic alignment switch (not shown) and to insert the alignment prism stop 223 in the optical path so as to perform the automatic alignment.

MODIFIED EXAMPLE 1

Note that, the embodiments described above relate to the eye refractive power measurement apparatus, but the present invention can be applied also to other ophthalmologic apparatus such as a fundus camera, a tonometer, a corneal shape measurement apparatus, a fundus blood flow meter, and a fundus tomographic image pickup apparatus (OCT) using near-infrared laser interference in the same manner. Here, when a fundus tomographic image is displayed in a predetermined frame of a display portion, there is a case where the fundus tomographic image is tilted with respect to the frame. In this case, by moving a position of the optical axis of the apparatus with respect to the eye to be inspected, the fundus tomographic image can be displayed substantially in a symmetric manner with respect to the vertical direction in the frame. When the above-mentioned movement is performed, it is preferred to perform the drive change of the joystick according to the embodiments of the present invention. In addition, it is possible to use a result of segmentation of layers in the fundus tomographic image for automatically detecting a tilt of the fundus tomographic image, and to automatic perform the drive change of the joystick according to the embodiments of the present invention when the tilt is detected.

MODIFIED EXAMPLE 2

As an informing unit for informing the inspector that the measuring mode is the second mode in which the drive direction is changed, any form of informing unit can be used without limiting to the icon display in a corner of the monitor in the above-mentioned embodiments of the present invention. However, it is more preferred to use an informing unit that informs the inspector visually or in an auditory manner.

MODIFIED EXAMPLE 3

In addition, it is possible to provide a selection unit for selecting whether or not to perform the drive change for driving the first drive system to perform displacement in the up-down direction by the front-back tilting motion in the state where the automatic tracking control is performed as the second mode.

(Other Embodiments)

In addition, the present invention further provides an ophthalmologic control method, which includes an acquiring step of acquiring specific information of an eye to be inspected, and a control step of changing a motion of a joystick for moving an acquiring unit in an up-down direction from a rotation motion to a front-back tilting motion. Here, the joystick can perform a rotation motion for moving the acquiring unit in the up-down direction, a left-right tilting motion for moving the acquiring unit in a left-right direction with respect to the eye to be inspected, and a front-back tilting motion for moving the acquiring unit in a front-back direction with respect to the eye to be inspected.

Further, as an ophthalmologic control program, the following process may be performed. Specifically, software (program) for realizing the functions of the embodiments described above is supplied to a system or an apparatus via a network or an arbitrary type of storage medium, and a computer (CPU or MPU) of the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-279584, filed Dec. 21, 2011, which is hereby incorporated by reference herein in its entirety.

What is claimed is:

1. An ophthalmologic apparatus, comprising:
   an acquiring unit configured to acquire specific information of an eye to be inspected;
   a joystick which can perform a rotation motion for moving the acquiring unit in an up-down direction, a left-right tilting motion for moving the acquiring unit in a left-right direction with respect to the eye to be inspected, and a front-back tilting motion for moving the acquiring unit in a front-back direction with respect to the eye to be inspected; and
   a control unit configured to change a moving direction of the acquiring unit, performed in response to the front-back tilting motion of the joystick, from the front-back direction to the up-down direction.

2. An ophthalmologic apparatus according to claim 1, wherein the control unit is configured to inhibit the acquiring unit from being moved in response to the rotation motion of the joystick after the control unit changes the moving direction of the acquiring unit, performed in accordance with the front-back tilting motion of the joystick, from the front-back direction to the up-down direction.

3. An ophthalmologic apparatus, comprising:
   an acquiring unit configured to acquire specific information of an eye to be inspected;
   a joystick which can perform (a) input for displacement in an up-down direction by a first motion of rotation, (b) input for displacement in a left-right direction by a second motion of left-right tilting, and (c) input for displacement in a front-back direction by a third motion of front-back tilting;
   a first drive system, a second drive system, and a third drive system configured to drive the acquiring unit in the up-down direction, the left-right direction, and the front-back direction in response to the first motion, the second motion, and the third motion of the joystick, respectively, so as to displace the acquiring unit with respect to the eye to be inspected; and a control unit configured to drive and control the first drive system, the second drive system, and the third drive system, wherein:

(1) the control unit has a first mode and a second mode;

(2) in the first mode, the control unit drives the first drive system, the second drive system, and the third drive system in response to the first motion, the second motion, and the third motion of the joystick, respectively; and (3) in the second mode, the control unit inhibits driving of the first drive system in response to the first motion, controls the second drive system to drive in response to the second motion, and controls the first drive system to drive in response to the third motion.

4. An ophthalmologic apparatus according to claim 3, wherein in the second mode, the control unit automatically controls the third drive system independently of the joystick, and performs automatic tracking control in the front-back direction.

5. An ophthalmologic apparatus according to claim 4, further comprising a selection unit configured to select whether to perform a drive change so that the first drive system is driven in response to the third motion or not to perform the drive change so that the third drive system is driven in response to the third motion, in a state where the automatic tracking control is performed as the second mode.

6. An ophthalmologic apparatus according to claim 3, further comprising an input unit configured to switch from the first mode to the second mode, wherein after driving in the front-back direction in response to the joystick being moved in the third motion, a drive change via the input unit is performed to provide driving in the up-down direction in response to the joystick being moved in the third motion.

7. An ophthalmologic apparatus according to claim 6, wherein the second mode is performed in a state where transillumination observation of pupil of the eye to be inspected is performed.

8. An ophthalmologic apparatus according to claim 3, wherein the control unit has a third mode as an automatic alignment mode, and in the third mode, the control unit automatically controls the first drive system, the second drive system, and the third drive system independently of the joystick until aligned states of the acquiring unit with respect to the eye to be inspected in the up-down direction, the left-right direction, and the front-back direction become constant, respectively.

9. An ophthalmologic apparatus according to claim 8, wherein in accordance with one of (a) when the specific information of the eye to be inspected cannot be obtained correctly by the acquiring unit in the third mode, and (b) when the joystick is operated in the third mode, the control unit automatically changes from the third mode to the second mode.

10. An ophthalmologic apparatus according to claim 3, wherein the control unit includes an informing unit configured to inform an inspector that a current mode is the second mode.

11. An ophthalmologic apparatus according to claim 10, wherein the informing unit informs the inspector visually or in an auditory manner.

12. An ophthalmologic apparatus according to claim 3, wherein the control unit stops the second mode one of (a) when the acquiring unit has been displaced in the front-back direction beyond a predetermined range with respect to the eye to be inspected, and (b) when an operation other than a predetermined operation is performed.

13. An ophthalmologic control method, comprising:

an acquiring step of acquiring, by an acquiring unit, specific information of an eye to be inspected; and a control step of changing a motion of a joystick, which can perform a rotation motion for moving the acquiring unit in an up-down direction, a left-right tilting motion for moving the acquiring unit in a left-right direction with respect to the eye to be inspected, and a front-back tilting motion for moving the acquiring unit in a front-back direction with respect to the eye to be inspected, so that a moving direction of the acquiring unit, performed in response to the front-back tilting motion of the joystick, is changed from the front-back direction to the up-down direction.

14. A medium for storing an ophthalmologic control program for causing a computer to perform the acquiring step and the control step of the ophthalmologic control method according to claim 13.

\* \* \* \* \*